United States Patent [19]

Engel et al.

[11] Patent Number: 4,643,995

[45] Date of Patent: Feb. 17, 1987

[54] ANALGESIC PYRIDINE-2-ETHERS OR PYRIDINE-2-THIOETHERS HAVING A NITROGEN-CONTAINING CYCLOALIPHATIC RING

[75] Inventors: Jurgen Engel, Alzenau; Vladimir Jakovlev, Maintal; Bernd Nickel, Muhtal; Klaus Thiemer; Gerhard Scheffler, both of Hanau, all of Fed. Rep. of Germany

[73] Assignee: Degussa Aktiengesellschaft, Frankfurt am Main, Fed. Rep. of Germany

[21] Appl. No.: 682,773

[22] Filed: Dec. 17, 1984

[30] Foreign Application Priority Data

Dec. 28, 1983 [DE] Fed. Rep. of Germany ....... 3347276

[51] Int. Cl.$^4$ ..................... A61K 31/55; C07D 401/12
[52] U.S. Cl. .................... 514/210; 514/212; 514/304; 514/305; 514/318; 514/340; 514/343; 540/1; 540/481; 540/597; 546/125; 546/133; 546/193; 546/194; 546/275; 546/281; 546/291; 546/296; 546/297; 546/298; 546/299; 546/300
[58] Field of Search ............. 546/193, 296, 194, 297, 546/133, 291, 125, 298, 281, 299, 275, 300; 260/244.4; 514/318, 304, 305, 340, 343, 210, 212; 540/1, 481, 597

[56] References Cited

U.S. PATENT DOCUMENTS

| | | | |
|---|---|---|---|
| 3,370,059 | 2/1968 | Schuler et al. | 546/193 |
| 3,905,984 | 9/1975 | Durant et al. | 546/332 X |
| 3,946,024 | 3/1976 | Fleckenstein et al. | 546/193 |
| 3,947,463 | 3/1976 | Fleckenstein et al. | 546/193 |
| 3,954,782 | 5/1976 | Fleckenstein et al. | 546/193 |
| 3,956,294 | 5/1976 | Fleckenstein et al. | 546/193 |
| 3,980,659 | 9/1976 | Fleckenstein et al. | 546/193 |
| 4,061,642 | 12/1977 | Fleckenstein et al. | 546/193 |
| 4,243,807 | 1/1981 | Friebe et al. | 546/232 |
| 4,288,442 | 9/1981 | Friebe et al. | 546/199 X |
| 4,409,228 | 10/1983 | Nisato et al. | 546/193 |

FOREIGN PATENT DOCUMENTS

| | | | |
|---|---|---|---|
| 630125 | 10/1963 | Belgium | 546/193 |
| 21973 | 1/1981 | European Pat. Off. | 546/193 |

OTHER PUBLICATIONS

*Chemical Abstracts*, 96:122808x (1982)[EP No. 40,696, Baldwin et al., 12/2/81].

*Primary Examiner*—Richard A. Schwartz
*Attorney, Agent, or Firm*—Cushman, Darby & Cushman

[57] ABSTRACT

There are disclosed pyridine-2-ethers and pyridine-2-thioethers having a nitrogen-containing cycloaliphatic ring corresponding to the formula

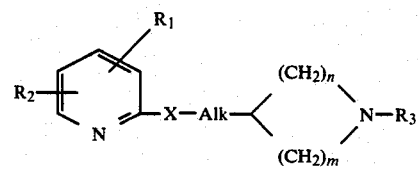

the pyridine-N-oxides and/or amine oxides thereof and the pharmaceutically acceptable salts thereof. The compounds show analgesic activity.

13 Claims, No Drawings

ANALGESIC PYRIDINE-2-ETHERS OR PYRIDINE-2-THIOETHERS HAVING A NITROGEN-CONTAINING CYCLOALIPHATIC RING

BACKGROUND OF THE INVENTION

Pyridine derivatives corresponding to the following general formula

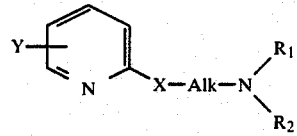

and the salts thereof are known from Belgian Pat. No. 630125 and related Schuler U.S. Pat. No. 3,370,059. In this formula $R_1$ and $R_2$ represent alkyl radicals, preferably those which are connected to a ring which can contain a further hetero atom, more particularly oxygen. Alk represents a straight or branched lower alkylene chain having at most 4 carbon atoms, X represents sulphur, oxygen or an NH group. Y can represent a halogen, preferably at the 3-position, an alkyl, trihalomethyl or alkoxy group, or the radical —CN, —COOR or —CONR$_3$R$_4$, R, R$_3$ and R$_4$ being the the same or different and representing hydrogen or lower alkyl groups.

The corresponding sulphones and sulphoxides of the above compounds are also known from Belgium Pat. No. 650361 (X represents SO or SO$_2$ in the above formula).

These compounds have an analgesic or antiphlogistic effect.

4-Amino-1-(2-pyridyl)-piperidines corresponding to the following formula and the pharmaceutically-acceptable salts thereof.

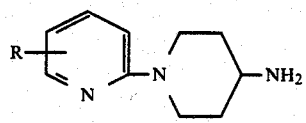

wherein R represents hydrogen, halogen, methyl, trifluromethyl, lower alkoxy, trifluoromethoxy, 2,2,2-trifluoroethoxy, lower alkylthio, trifluoromethylthio, phenoxy, a phenoxy group which is substituted in the phenyl nucleus by halogen, trifluoromethyl, lower alkyl, lower alkoxy, lower alkylthio or cyano, phenylthio or a phenylthio group which is substituted in the phenyl nucleus by halogen, trifluoromethyl, lower alkyl, lower alkoxy, lower alkylthio or cyano, are also known from European Patent Application No. 21973 and related U.S. Pat. No. 4,409,228.

These compounds have an appetite-suppressant effect.

Pyridine compounds corresponding to the following general formula are described in German Offenlegungsschrift No. 22 30 392 and related U.S. Pat. Nos. 3,946,024; 3,947,463; 3,954,782; 3,956,294; 3,980,659, and 4,061,642

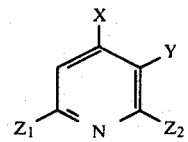

wherein X represents an optionally branched and/or substituted alkyl, optionally branched and/or substituted alkenyl, optionally substituted cycloalkyl, aralkyl, aryl group or a heterocyclic radical, or, if Y is other than hydrogen, also hydrogen, Y is a cyano, amino, nitroso, nitro, an optionally branched and/or substituted alkyl, optionally branched and/or substituted alkenyl, optionally substituted cycloalkyl, or aralkyl group or a radical

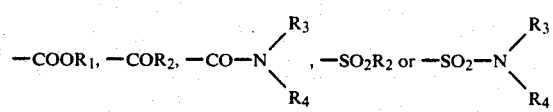

or, if X is other than hydrogen, also hydrogen, $Z_1$ represents inter alia the radicals —OR$_{12}$, SR$_{12}$ or —SO$_2$R$_{12}$, $Z_2$ represents inter alia a chlorine or bromine atom, a cyano, hydroxy or mercapto group and R$_1$ and R$_2$ represents an optionally branched and/or substituted alkyl, or an optionally branched and/or substituted alkenyl group, R$_2$ can also represent an optionally substituted cycloalkyl, aralkyl, aryl or heterocyclic group, R$_3$ and R$_4$ represent hydrogen, an optionally branched and/or substituted alkyl, or optionally substituted cycloalkyl, aralkyl or aryl group, and the alkyl radicals R$_3$ and R$_4$ can also be directly linked or linked via a hetero atom and R$_{12}$ represents an optionally branched and/or substituted alkyl, an optionally branched and/or substituted alkenyl, an optionally substituted cycloalkyl, aralkyl or aryl group.

These compounds are intermediate products, particularly for the production of dyes. Moreover, it should be noted that these compounds are of importance as pesticides and for pharmaceutical purposes.

SUMMARY OF THE INVENTION

The present invention relates to pyridine-2-ethers and pyridine-2-thioethers having a nitrogen-containing cycloaliphatic ring and corresponding to the formula

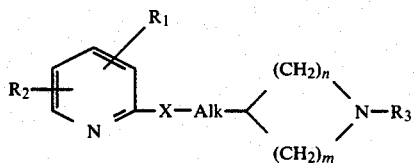

the pyridine-N-oxides and/or amine oxides thereof and the pharmaceutically acceptable salts thereof, in which the radicals R$_1$ and R$_2$ represent, for example, hydrogen, halogen atoms, a trifluoromethyl group, a cyano group, a nitro group, an amino group, a mono-C$_1$-C$_6$-alkylamino group, a di-C$_1$-C$_6$-alkylamino group, an amino group which is substituted by a phenyl radical, a mono- or di-halophenyl radical or a phenyl-C$_1$-C$_4$-alkyl radical, a C$_1$-C$_6$ alkanoyl amino group, a C$_1$-C$_6$ alkoxycarbonylamino group, a C$_1$-C$_6$ alkyl group which is optionally substituted by a phenyl radical, a phenyl group, a hydroxy group, a $C_1-C_6$ alkoxy group, a phenoxy group, a carboxy group, a carb-$C_1-C_6$ alkoxy group or a carbamoyl group which is optionally substituted by one or two $C_1-C_6$ alkyl groups, the radical $R_3$ represents, for example, hydrogen, a $C_1-C_6$ alkyl group, a $C_3-C_6$ alkenyl group, a $C_3-C_6$-alkynyl group, a $C_3-C_7$ cycloalkyl group, a $C_5-C_7$ cycloalkenyl group, a phenyl-$C_1-C_4$-alkyl group, a carb-$C_1-C_6$-alkoxy group or a $C_2-C_6$ alkanoyl group which is optionally substituted by a $C_3-C_6$ cycloalkyl, radical or a $C_1-C_4$ alkyl group which contains on the same carbon atom two $C_1-C_6$ alkoxy groups or a $C_2-C_4$ alkylene dioxy group or wherein $R_3$ represents a $C_1-C_6$ alkyl group which is mono- or di-substituted by $C_3-C_7$ cycloalkyl groups, hydroxy groups, $C_1-C_6$ alkoxy groups, halogen atoms, sulpho groups ($-SO_3H$), amino groups, $C_1-C_6$ alkylamino groups, di-$C_1-C_6$-alkylamino groups, $C_1-C_6$ alkylcarbonyl groups, $C_3-C_7$ cycloalkylcarbonyl groups, carb-$C_1-C_6$-alkoxy groups or a benzoyl group, in which X represents oxygen, sulphur, SO, or $SO_2$, Alk represents alkylene having from 0 to 4 carbon atoms and n and m are the same or different and can be from 1 to 3, and n can also be 0, if Alk has at least one carbon atom and in this case m is from 2 to 6 and the group

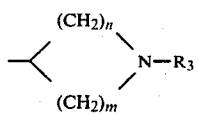

can also represent a quinuclidyl radical or a tropanyl radical, the pyridine-N-oxides and/or amine oxides thereof and the pharmaceutically acceptable salts thereof and a process for the production thereof. One class of compounds has the formula

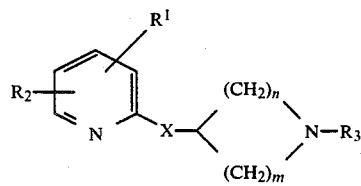

wherein $R_1$ is hydrogen, amino or $C_2-C_6$-alkanolamino, $R_2$ is chlorine, bromine, fluorine, $C_1-C_4$-alkyl or $C_1-C_4$-alkoxy, X is sulphur and $R_3$ is hydrogen, $C_3-C_6$-alkenyl, $C_1-C_6$-alkyl or $C_1-C_6$-alkyl substituted with a halogen atom, a methylenedioxy group or one or two hydroxy groups, and wherein the basic saturated ring

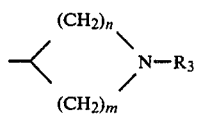

is a pyrrolidyl group, a piperidyl group or a homopiperidyl group which in each case on the N-atom contains the group $R_3$ and pharmaceutically acceptable salts thereof. In the formula just referred to a more limited group is one wherein $R_1$ is hydrogen, $R_2$ is chlorine, bromine, or fluorine and $R_3$ is hydrogen or a $C_1-C_6$-alkyl group.

The compounds of formula I can be prepared by reacting a compound corresponding to formula

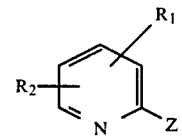

or the pyridine-N-oxides thereof with a compound corresponding to the general formula

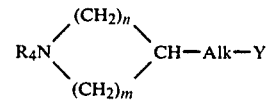

wherein $R_4$ is as defined for $R_3$ or may also represent the group S and S is a conventional amino protecting group and Y represents a halogen atom, a $C_1-C_6$ alkyl-sulphonyloxy group or an arylsulphonyloxy group if Z in formula II is a hydroxy group or a mercapto group, or wherein Y represents a hydroxy group or a mercapto group if Z in formula II is a halogen atom, and a group S, if present, is split off and/or in the compounds corresponding to formula I the radical $R_1$; $R_2$ and $R_3$ are converted into other possible definitions therefore and/or compounds corresponding to formula I, wherein the radicals $R_1$ to $R_3$ and Alk X, n and m are as defined above, are converted into the corresponding sulphones, sulphoxides, amino-oxides or pyridine-N-oxides.

In the above formula I when there is present halogen or halophenyl, the halogen for example, can be chlorine, bromine, or fluorine. Examples of mono $C_1-C_6$-alkylamino groups are methylamino, ethylamino, propylamino, isopropylamino, butylamino, sec.-butylamino, hexylamino. Examples of di-$C_1-C_6$ alkylamino groups are dimethylamino, diethylamino, methyl ethyl amino, dipropylamino, dibutylamino, and dihexylamino.

Examples of $C_1-C_6$ alkanoyl amino groups are formamido, acetamido, propionamido, butyramido.

Examples of alkoxycarbonylamino groups are methoxycarbonylamino, ethoxycarbonylamino, propoxycarbonylamino.

Examples of $C_1-C_6$ alkyl groups are methyl, ethyl, propyl, isopropyl, butyl, sec.butyl, amyl, and hexyl.

Examples of $C_1-C_6$ alkoxy groups are methoxy, ethoxy, propoxy, isopropoxy, butyroxy, hexoxy.

Examples of carbo-$C_1-C_6$-alkoxy groups are carbomethoxy, carboethoxy and carbopropoxy.

Examples of $C_3-C_6$-alkenyl and alkynyl groups are allyl, crotyl, methally, ethinyl, propinyl.

Examples of cycloalkyl groups are cyclopropyl, cyclobutyl, cyclopentyl, cyclohexyl, and cycloheptyl.

Examples of cycloalkenyl groups are cyclopentenyl, cyclohexenyl, and cycloheptenyl.

Examples of $C_2-C_6$ alkanoyl groups are acetyl, propionyl, butyryl, and hexanoyl.

Examples of $C_1-C_4$ alkyl groups substituted by two $C_1-C_6$-alkoxy groups are dimethoxymethyl, dimethoxyethyl, dihexoxymethyl diethoxyethyl, dibutoxyethyl.

Examples of alkylene dioxy groups are ethylenedioxy, propylenedioxy, butylenedioxy.

The compounds according to the invention are pharmacologically active. The present compounds have in particular a pronounced and powerful analgesic effect. They have, moreover, a hypotensive effect.

Thus, an object of the present invention is to provide compounds which have favorable pharmacological properties and are usable, as for example, medicines with analgesic activity.

The alkyl groups, alkenyl groups, alkynyl groups, alkoxy groups, alkanoylamino groups or alkanoyl groups, occuring in formula I can be straight or branched. This holds true for alkyl and alkoxy groups, if these are constituents of other combined groups (for example in the form of a monoalkyl-or-dialkyl-amino group, alkanoylamino group, alkoxycarbonylamino group, carbalkoxy group, alkylcarbonyl group and comparable groups). Likewise, in the phenyl-$C_1$-$C_6$alkyl radical (group) the alkyl-moiety can also be straight or branched if it consists of from 2 to 4 carbon atoms. The halogen atoms are chlorine, bromine or fluorine, particularly chlorine and fluorine. The alkyl and alkoxy groups as such or as a constituent of other combined groups consist in particular of from 1 to 4 carbon atoms, preferably 1 to 2 carbon atoms. The alkenyl groups or alkynyl groups preferably consist of 3 or 4 carbon atoms. Alkanoyl groups or alkanoylamino groups consist in particular of from 2 to 4, preferably from 2 to 3 carbon atoms. The alkyl moiety of the phenyl-$C_1$-$C_4$-alkyl radical (group) consists in particular of from 1 to 3, preferably 1 to 2 carbon atoms. The $C_3$-$C_7$-cycloalkyl group consists in particular of from 5 to 6 carbon atoms, the $C_5$-$C_7$-cycloalkenyl group consisting in particular of from 5 to 6 carbon atoms. The $C_2$-$C_4$-alkylene dioxy group consists in particular of from 2 to 3 carbon atoms. The group

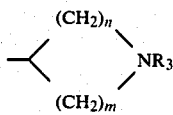

forms in particular a 5-, 6- or 7-membered ring.

The following are examples thereof: piperidine ring (piperidyl-(4)-, piperidyl-(3)- or piperidyl-(2)-ring), homopiperidine ring (for example homopiperidyl-(4)-ring), pyrrolidine ring (pyrolidyl-(2)- or pyrrolidyl-(3)-ring).

The quinuclidine ring is preferably a quinuclidyl-(3)-radical and the tropanyl ring is preferably the tropanyl-(3) radical.

X preferably sulphur.

Particularly important compounds corresponding to formula I are those in which X represents sulphur, one of the radicals $R_1$ or $R_2$ represents hydrogen, the saturated nitrogen-containing ring is a piperidyl radical which is directly bound to the sulphur atom, Alk=0 carbon atoms, that is Alk is not present and $R_3$ represents hydrogen, a $C_3$-$C_6$ alkenyl group (straight or branched) or a straight or branched $C_1$-$C_6$ alkyl group which can also contain on the carbon atom at the end position two $C_1$-$C_4$ alkoxy groups or a $C_2$-$C_4$ alkylene dioxy group. In this instance, the pyridine ring preferably contains a substituent corresponding to the above definition of $R_1/R_2$, this substituent preferably being a halogen atom (for example chlorine) which is located in particular at the 6-position of the pyridine ring.

The process for the production of compounds corresponding to formula I from compounds corresponding to formulae II and III is carried out in a solvent or dispersant at a temperature of from 20° to 200° C., preferably from 40° to 150° C., particularly from 50° to 120° C. The following are possible examples of solvents of dispersants: lower aliphatic alcohols (from 1 to 6 carbon atoms, e.g. methanol, ethanol, hexanol); propanol, isopropanol, butanol, lower aliphatic ethers, (e.g., diethylether, diisopropylether), aromatic hydrocarbons, (e.g. benzene, toluene xylene), cyclic ethers (e.g., dioxane, tetrahydrofuran), esters of low aliphatic carboxylic acids with low aliphatic alcohols, e.g. ethyl acetate, amides and N-alkyl-substituted amides of aliphatic $C_1$-$C_6$ carboxylic acids (e.g. dimethylformamide, dimethylacetamide), $C_1$-$C_6$ dialkylsulphoxides (e.g., dimethylsulphoxide) and further aprotic agents, such as N-methylpyrrolidine, tetramethyl-urea, hexamethylphosphoric acid triamide, acetonitrile. The individual alkyl radicals of the above solvents contain, for example from 1 to 6, in particular from 1 to 4 carbon atoms.

The process is suitably carried out in the presence of condensing agents. The following are examples of such condensing agents: inorganic condensing agents, such as alkali metal or alkaline earth metal hydroxides, e.g. sodium hydroxide, potassium hydroxide, calcium hydroxide, alkali metal hydrides, e.g. sodium hydride, alkali metal amides, alkali metal or alkali earth metal carbonates, e.g. sodium carbonate or organic bases, e.g. sodium carbonate such as pyridine, tertiary amines, e.g. triethylamine, piperidine, alkali metal alcoholates, e.g. sodium ethylate, alkali metal acetates, e.g. sodium acetate, or also triethyl phosphate. The alkali metals are particularly sodium or potassium. The process can also be carried out under phase-transfer conditions (that is with the addition of one or more long-chain amines, such as a benzyl-tributyl ammonium halide, a tetrabutyl-ammonium halide or benzyl-triphenyl-phosphonium chloride.)

The corresponding salt is generally first produced from the starting component which contains the hydroxy or mercapto group using an alkali metal compound as referred to above and is then reacted with the second reaction component. A starting component corresponding to formula III can also be used which contains a conventional amino protecting group instead of the radical $R_3$, which protecting group is readily separable on completion of the reaction by solvolysis or hydrogenation. Some definition of $R_3$ (for example benzyl, alkoxycarbonyl) may even represent such protective groups. Subsequent separation is of course not necessarily required with these groups.

If Y in formula III represents a $C_1$-$C_6$ alkyl-sulphonyloxy group, it is preferably a group with from 1 to 4 carbon atoms in the alkyl moiety (for example the methyl sulphonyloxy group). If Y in formula III represents an arylsulphonyloxy group, the aryl radical is preferably a phenyl or naphthyl radical which can optionally be substituted by $C_1$-$C_4$ alkyl radicals (in particular methyl radicals) (for example a p-toluene sulphonyloxy group).

Production of starting materials corresponding to formula II, wherein Z represents SH: such compounds can be produced, for example, from compounds corresponding to formula II, in which Z represents a halogen atom (fluorine, chlorine, bromine, iodine) by reacting with sodium or potassium mercaptide in alcohols (e.g. methanol, ethanol, propylene glycol) at a temperature of from 20° to 150° C. or even in aqueous medium at from 100° to 150° C. or by reacting with thiourea in lower alcohols (e.g. ethanol, isopropanol) at a temperature of from 20° to 100° C. and subsequent alkaline decomposition (for example with aqueous sodium carbonate on a steam bath). A further possibility is to heat compounds corresponding to formula II, in which Z represents a hydroxy group, with phosphorus pentasulphide to a temperature of from 50° to 200° C., for example from 60° to 160° C. These reactions can be carried out analogously to the processes given, for example in Erwin Klingenberg, Pyridine and its Derivatives, Part IV (1964), page 348–351 or in DE-OS No. 2 230 392, page 9 or the related United States patents mentioned above.

Starting materials corresponding to formula III, in which Y represents a hydroxy group and $R_3$ represents hydrogen by introducing the radical $R_3$ by N-alkylation, N-acylation as well as by addition of suitable a-B-unsaturated compounds in known manner or under the conditions given in this application for the introduction of the radical $R_3$ to compounds corresponding to formula I in which $R_3$ represents H. Those compounds corresponding to formula III, in which $R_3$ is hydrogen, can be obtained from compounds corresponding to formula III, in which $R_3$ is methyl group (the other radicals or symbols can be as defined above) by reacting with chloroformic acid ethylester and subsequently separating the carbethoxy group (the reaction conditions are identical to those described in this application for the analogous reactions of compounds corresponding to formula I).

Those starting materials corresponding to formula III in which Y is a halogen atom can be obtained from compounds by reacting, for example, with thionylhalides (chlorides, bromides, iodides) or sulphonic acid chlorides in halogenated hydrocarbons (chloroform) or aromatic hydrocarbons (benzene) or in pyridine at a temperature of the solvent used). The starting materials corresponding to formula III, in which Y represents an alkyl-sulphonyloxy group or an arylsulphonyloxy group can be obtained for example, from the appropriate hydroxy compounds (Y=OH) by reacting with $C_1$-$C_6$ alkylsulphonic acid chlorides in inert solvents conventionally used for this purpose (benzene, toluene, xylene, chloroform, methylene chloride, dioxane) at a temperature of from 20° to 150° C. The process is effectively carried out in the presence of an acid-binding material (for example tertiary amines, such as triethylamine).

If $R_3$ is hydrogen, the N-atom can be protected by an easily-separable protecting group.

Starting materials corresponding to formula III, in which Y is a mercapto group, can be obtained from the halides corresponding to formula III (Y=halogen) by reacting with alkali metal sulphides. These reactions can be carried out as in C. Ferri, Reaktionen der organischen Synthese 1978, pages 205–209 or as in DE-OS No. 2 230 392, for example page 9 or in the related United States patents.

Starting materials corresponding to formula III have the following structure.

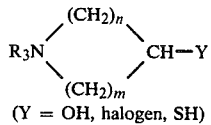

(Y = OH, halogen, SH)

can be obtained for example in the following manner:

The radical $R_3$, as is described below is introduced by alkylation or acylation into a compound corresponding to formula IIIa, in which $R_3$ is hydrogen and the group CHY has the structure C=O: The compound obtained in this manner

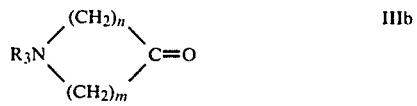

can then be reacted with hydrogen sulphide as in H. Barrera and R. E. Lyle, J. Org. Chem 27 (1962), pages 641–643 and then reduced with sodium borohydride to produce compound IIIa, in which Y represents SH.

However, in a compound corresponding to IIIb it is possible to reduce the keto group in known manner with alkali metal boranates (Na, K, L) or other complex metal hydrides, (for example lithium aluminum hydride) to produce the hydroxy group (c.f. Houben-Weyl, Methoden der Organischen Chemie, Volume 4/1d, 1982, pages 271 et seq), substitute a chlorine atom for the hydroxy group using conventional chlorinating agents, (for example thionyl chloride, sulphuryl chloride) (c.f. Houben-Weyl, Methoden der Organischen Chemie, Volume 5/3 1962, pages 862–912), produce the corresponding Grignard compound (formula IIIa, Y=MgCl) from the resulting chloride with magnesium (c.f. Houben-Weyl, Methoden Organischen Chemie, Volume 13/2a, 1973, pages 53–85) and produce the mercapto compound IIIa, in which Y represents SH, from such a Grignard compound using a sulphur or thionyl chloride (c.f. Houben-Weyl, Methoden der Organischen Chemie, volume 9, 1955, page 19; E. E. Reid, Organic Chemistry of Bivalent Sulfur Volume: Chem Publ Corp, New York, 1958, page 37).

If desired, the radical $R_3$ (methyl radical or acyl radical) can again be separated in conventional manner.

Starting materials corresponding to formula IIIa, wherein y represents a hydroxy group $R_3$ and represents hydrogen can also be obtained for example from the corresponding hydroxy pyridines by reduction with sodium or catalytically-activated hydrogen (optionally under pressure, for example up to 100 bars) at a temperature of 20° to 150° C. (solvent: $C_1$-$C_6$-alcohols). The radical $R_3$ can be introduced into these compounds as described in the following.

The radicals $R_1$, $R_2$, and $R_3$ of compounds corresponding to formula I can be converted into other meanings by the following reactions for example:

1. By alkylation or acylation: This is in particular the introduction of the radical $R_3$ into compounds corresponding to formula I, wherein $R_3$ represents hydrogen, but is also the acylation or alkylation of amino groups (if, for example, $R_1$ and $R_2$ are amino groups). Alkylation is, for example, effected by reacting with compounds corresponding to the formula R'Hal, $ArSo_2OR'$ and $SO_2(OR')_2$, and Hal is a halogen atom (in particular chlorine, bromine or iodine) and Ar is an aromatic radical (for example a phenyl or naphthyl radical which is optionally substituted by one or more low alkyl radicals) and R' can be as defined for $R_3$ (with the exception of hydrogen). The following are examples thereof: p-toluene sulphonic acid-$C_1$-$C_6$-alkylesters, $C_1$-$C_6$-dialkysulphates, $C_1$-$C_6$-alkylhalides, $C_3$-$C_6$-alkenylhalides, $C_3$-$C_6$-alkynylhalides, $C_3$-$C_7$-cycloalkylhalides, $C_5$-$C_7$-cycloalkenylhalides and the like. In the above compounds the alkyl group can in each case be substituted in accordance with the definition of $R_3$. If $R_3$ is a $C_1$-$C_6$ alkyl group containing at least one hydroxy group (at the 2 position), alkylation can be carried out by a suitable $C_1$-$C_6$ alkylene oxide compound which can of course contain further substituents corresponding to the defintion of $R_3$. The alkylation and acylation reaction is optionally carried out with addition of conventional acid-binding agents, such as alkali metal hydroxides, alkali metal carbonates, alkali metal hydrogencarbontes, alkaline earth metal carbonates, alkali metal acetates, tertiary amines (for examples trialkyl amines, such as triethyl amine), pyridine or even alkali metal hydrides at a temperature of from 0° to 200° C., preferably from 40° to 140° C., in inert solvents or suspension agents. The following are examples of solvents or dispersants which can be used: aromatic hydrocarbons, such as benzene, toluene, xylene; aliphatic ketones, such as acetone, methylethylketone; halogenated hydrocarbons, such as chloroform, carbon tetrachloride, chlorobenzene, methylene chloride; aliphatic ethers, such as butylether; cyclic ethers such as tetrahydrofuran, dioxane; sulphoxides such as dimethyl sulphoxide; tertiary acid amides, such as dimethyl formamide, N-methyl pyrrolidone hexamethyl phosphoric acid triamide; aliphatic alcohols, such as methanol, ethanol, isopropanol, amyl alcohol, tert.-butanol, cycloaliphatic hydrocarbons, such as cyclohexane and the like. Aqueous mixtures of the above solvents can also be used. The process is often carried out at the reflux temperature of the solvents or dispersants used. The components of the alkylation reaction are often used in excess. Alkylation can also be carried out in the presence of tetraalkyl ammonium salts (in particular of the halides) combined with alkali metal hydroxides at a temperature of from 0° to 100° C., preferably from 20° to 80° C. in an aprotic solvent or even in chloroform or methylene chloride. The following are particular examples of aprotic solvents which can be used: tertiary amides (dimethylformamide, N-methyl pyrrolidone, hexamethylphosphoric acid triamide), dimethyl sulphoxide, acetonitrile, dimethoxyethane, acetone, tetrahydrofuran). During acylation a $C_2$-$C_6$ alkanoyl group which has optionally been substituted by a $C_3$-$C_6$ cycloalkyl radical or a carb-$C_1$-$C_6$-alkoxy group is introduced for example into those compounds corresponding to formula I, in which $R_3$ represents hydrogen. The process is thus carried out in known manner, preferably using carb-$C_1$-$C_6$-alkoxy halides (or the corresponding anhydrides) or using $C_2$-$C_6$ alkanoyl halides (or corresponding anhydries), in which the alkanoyl group can also be substituted by a $C_3$-$C_6$ cycloalkyl radical. The reaction temperature is preferably from 30° to 120° C. Alkyation and acylation can also optionally be carried out by first producing an alkali metal compound (for example, a sodium, potassium or even lithium salt) from the compound to be alkylated or acylated by reacting it in an inert solvent such as dioxane, dimethyl formamide, benzene or toluene, with an alkali metal, alkali metal hydride or alkali metal amides (in particular sodium or sodium compounds) or butyl lithium at a temperature of from 0° to 150° C. and then adding the alkylating agent.

Other chemically-equivalent agents which are conventionally used in chemistry can also be used instead of the above alkylating and acylating agents (c.f., by way of example, also L. F. and Mary Fieser "Reagents for Organic Synthesis", John Wiley and Sons, Inc., New York, 1967, volume 1, pages 1303–1304 and volume 2, page 471. $C_3$-$C_6$ alkenyl groups which have a $C_1$-$C_6$ alkylcarbonyl group, a carb-$C_1$-$C_6$-alkoxy group or a benzoyl group in the position adjacent to the double bond, can be added to compounds corresponding to formula I in which $R_3$ represents hydrogen. This reaction can be carried out in solvents at a temperature of suitable solvents: $C_1$-$C_6$ alkanols, aliphatic saturated ethers, aromatic hydrocarbons (benzene, toluene, xylene) chlorinated aliphatic hydrocarbons (methylene chloride, chloroform, dichloroethane).

3. The carb-$C_1$-$C_6$-alkoxy group can be introduced into those compounds corresponding to formula I, in which $R_3$ represents a methyl group, by reaction with haloformic acid-$C_1$-$C_6$-alkylesters or with phosgene, followed by a subsequent reaction with a $C_1$-$C_6$ alkanol. Chloroformic acid-$C_1$-$C_6$-alkylesters (for example chloroformic acid ethylesters) are preferably used.

These reactions are carried out in the presence of or in the absence of solvents or suspension agents at a temperature of from 20° to 180° C., preferably from 40° to 120° C. The following are examples of solvents for these reactions: aromatic hydroarbons (toluene, xylene), chlorinated hydrocarbons, such as methylene chloride or chloroform.

4. If the radical $R_3$ in compounds corresponding to formula I is a carb-$C_1$-$C_6$-alkoxy group or a $C_2$-$C_6$-alkanoyl group (optionally substituted by a cycloalkyl radical), these groups can be solvolytically split with formation of compounds corresponding to formula I, in which $R_3$ represents hydrogen. These groups are split in known manner, for example by saponification with acids (mineral acids, such as hydrochloric acid, sulphuric acid, in particular concentrated hydrohalic acids, such as HBr/glacial acetic acid) or using basic materials (potash, soda, aqueous alkali solutions, alcoholic alkali solutions, aqueous $NH_3$) at a temperature of from 10° to 150° C., more particularly from 20° to 100° C. If $R_3$ represents the group S and this group S is a solvolytically-removable protective group (for example: trifluoroacetyl radical, trityl radical, p-toluene sulphonyl radical, formyl radical, tert.-butyloxy carbonyl radical and the like), this group S is split off in the same manner.

If $R_3$ is a benzyl group, an a-phenylethyl group or is, as group S, another conventional protective group removable by hydrogenation these groups are suitably split by catalytic hydrogenation in the presence of conventional hydrogenation catalysts, in particular palladium catalyts, platinum oxide or even Raney Nickel, in a solvent or suspension agent, optionally under elevated pressure at a temperature of from 20° to 100° C., in particularly from 40° to 80° C. The following are examples of solvents or suspension agents which can be used: water, lower aliphatic alcohols, cyclic ethers, such as dioxan or tetrahydrofuran, aliphatic ethers, dimethylforamide etc, and mixture of these agents. The following are examples of protective groups which are removable by hydrogenation: a-arylakyl radicals, benzyl radicals which are substituted in the benzene nucleus (p-bromo- or p-nitrobenzyl radical), aralkoxy-carbonyl radicals, such as carbobenzoxy radical, carbobenzothio radical.

The protecting groups which are generally used in peptide synthesis are particularly suitable as the protecting groups S. Reference can be made inter alia to the book by Jesse P. Greenstein and Milton Winitz "Chemistry of Amino Acids", N.Y. 1961, John Wiley and Sons, Inc., volume 2, for example page 883 et seq.

5. If one or even both of the radicals $R_1$, $R_2$ represents a nitro group, this can be reduced to the corresponding amino group. A catalytic hydrogenation is particularly suitable for this reduction. The following are examples of suitable catalysts: Raney nickel, noble metals, such as palladium and platinum and compounds thereof with and without carriers, such as barium sulphate, calcium sulphate etc. It is advisable to hydrogenate the nitro group at a temperature of from 20° to 80° C. and under a pressure of from about 5 to 50 excess atmosphere guage in a solvent, for example alcohols, dioxane tetrahydrofuran etc. It may be advantageous for the subsequent isolation of the reduced compounds to add a dehydrating agent, such as anhydrous sodium- or magnesium sulphate at the outset to the mixture to be hydrogenated. The reduction can, however, also be carried out with nascent hydrogen, for example zinc/hydrochloric acid, tin/hydrochloric acid, iron/hydrochloric acid or using salts of hydrogen sulphide in alcohol/water at a temperature of from about 70° to about 120° C. or with activated aluminum in aqueous ether at from 20° to 40° C. or with tin (II)-chloride/hydrochloric acid.

6. Activated halogen atoms in the pyridine ring can, for example, be replaced by other radicals, or an amino group which is optionally substituted by phenyl or halophenyl or phenyl-$C_1$-$C_6$-alkyl. This reaction can, for example, be carried out in an inert solvent or suspension agent, such as tetrahydrofuran, dioxane, low alkanols (ethanol, n-propanol), dimethyl sulphoxide or dimethyl formamide or even in the presence of an excess of the basic reaction constituent at a temperature of from 50° to 200° C., preferably from 80° to 130° C. Acid acceptors, such as potash, sodium carbonate, calcium carbonate or non-quartenizing tertiary amines such as diisopropyl methyl amine can also be added during the reaction. Halogen atoms at the 3-,4- or 5-position of the pyridine ring are suitable for this if they are activated by, for example, a nitro group.

The compounds corresponding to formula I can be converted into the corresponding amine-oxides (for example oxidation of the N-atom at which the radical $R_3$ is located) and/or the pyridine-N-oxides, for example, in inert solvents, such as chloroform or other chlorinated hydrocarbons, benzene, toluene, acetone, dilute acetic acid or acetic acid ethyl ester with hydrogen peroxide, a conventional aliphatic or aromatic peracid (peracetic acid, perbenzoic acid, m-chloroperbenzoic acid) or other mono-substituted products of hydrogen peroxide, such as alkali metal peroxides or alkyl peroxides (such as tert.-butyl peroxide) at a temperature of from 0° to 150° C., preferably from 0° to 100° C. If X represents S, the corresponding sulphoxides or sulphones are firstly produced by this reaction. However, these are then oxidized to produce the same oxides.

The compounds corresponding to formula I, in which X represents a sulphur atom can also be converted in known manner by oxidation into those compounds in which X represents the group SO or $SO_2$. Hydrogen peroxide, dinitrogen tetraoxide, potassium permanganate, peracids (such as perbenzoic acid, chromic acid or other known oxidizing agents can, for example, be successfully used as oxidizing agents. The process is suitably carried out in the presence of water or solvents, such as alcohols, acetic acid (glacial acetic acid), acetic acid ethylester, benzene, acetone or chloroform. The lower alcohols, such as methanol or even acetic acid, are particularly suitable. The corresponding sulphoxide is generally obtained as the main product in addition to smaller quantities of the sulphone during oxidation with 30% hydrogen peroxide, peracids, nitric acid, nitrous gases (nitrogen dioxide), with cooling for example at a temperature of from $-20°$ C. to $+20°$ C. Furthermore, corresponding sulphoxides can be produced from compounds of formula I, in which X represents S, by oxidizing with chromic acid for (example in acetic acid solution at a temperature of from 50° to 100° C.), by oxidizing with iodosobenzene or by treating with bromine (for example in a halogenated hydrocarbon, such as chloroform or carbon tetrachloride with cooling and subsequently hydrolyzing the dibromo derivatives using water or dilute alkali. Regarding the reaction conditions and other oxidizing agents, reference is hereby made for example to Houben, Weyl, Methoden der Organischen Chemie, Volume IX (1955), pages 211–218. The oxidation of sulphides corresponding to formula I (X=S) with dimethyl sulphoxides at elevated temperature (from 150° to 180° C.) in accordance with J. Org. Chem. 23 (1958), pages 2028–2029 is also possible.

The sulphones and sulphoxides obtained in each case can be separated using conventional separation processes, for example by column chromatography on silica gel. The corresponding sulphone is obtained in relatively large yield or as the main product using more powerful oxidizing agents, such as potassium permanganate is acetic or aqueous sulphuric solution at a temperature of from 50° to 100° C. The compounds corresponding to formula I, in which X represents S or SO can for example, also be oxidized using hydrogen peroxide or peracids at elevated temperature, such as from 80° to 120° C. (in acetic acid anhydride, in the presence of phosphoric acid or any other inert agent generally used for this purpose), using chromic acid, using anodic oxidation or optionally also using sodium hypochlorite solutions (c.f. Houben-Weyl, Methoden der Organischen Chemie, Volume IX (1955), pages 227–231). A further possibility is to oxidize with organic hydroperoxides (for example alkyl hydroperoxides, such as tert.-butylhydroperoxide) in the presence of vanadium, molybdenum or titanium compounds (for example oxides of the above metals, such as molybdenum dioxide, vanadium pentoxide) in organic solvents, such as aromatic hydrocarbons (benzene), alkanols (ethanol) or esters of aliphatic carboxylic acids with alkanols (ethyl acetate) at a temperature of from 40° to 120° C., preferably from 50° to 80° C. according to Angewandte Chemie 78 (1966), page 937.

Those compounds corresponding to formula I contain asymmetric carbon atoms and generally occur in the form of racemates, can be resolved in known manner into the optically-active isomers using, for example, an opticallly-active acid. It is also possible to use from the beginning an optically-active starting material, a corresponding optically-active or diastereomeric form then being obtained as the end product.

The present invention thus also includes the D- and L-form and the DL-mixture when there is an asymmetric carbon atom in the compound corresponding to formula I and the corresponding diastereomeric forms in the case of two and more asymmetric carbon atoms.

The end products corresponding to formula I are obtained as free bases or in the form of the salts thereof, depending on the operating conditions and the starting materials. The salts of the end products can once again be converted in known manner into the free bases using, for example alkali or ion exchangers. Salts may be obtained from the latter by reacting with organic or inorganic acids, in particular those which are suitable for the formation of therapeutically-usable salts. The following can be used, for example as such acids: hydrohalic acids, e.g. hydrochloric acid and hydrobromic acid, sulphuric acid, phosphoric acid, nitric acid, perchloric acid, organic mono-di or tri-carboxylic acids of the aliphatic, alicyclic, aromatic or heterocyclic series and sulphonic acids. Examples are: formic, acetic, propionic, succinic, glycolic, latic, malic, tartaric, citric, ascorbic, maleic, fumaric, hydroxymaleic and pyruvic acid; phenylacetic, benzoic, p-aminosalicyclic, embonic acid, methane sulphonic, ethane sulphonic, hydroxyethane sulphonic, ethylene sulphonic acid; halobenzene sulphonic, e.g. chlorobenzene sulphonic, toluene sulphonic, e.g. toluene sulphonic, naphthalene sulphonic acid or sulphanlic acid or even 8-chloro-theophylline.

The present compounds are suitable for the production of pharmaceutical compositions. The pharmaceutical compositions or medicaments can contaain one or more of the present compounds. Conventional pharmaceutical carriers and auxiliaries can be used to produce the pharmaceutical preparations. The medicaments can be administered enterally, parenterally (for example intravenously, intramuscularly, subcutaneously) or orally. They can, for example, be dispensed in the form of tablets, capsules, pills, dragees, suppositories or plasters. The following are examples of liquids: oily or aqueous solutions or suspensions (in, for example, sesame or olive oil), emulsions, injectable aqueous or oily solutions or suspensions. Furthermore, dry ampoules which contain as active material the present compound I, for example, can be produced and before the use contents, of the dry ampoule is dissolved in water, physiocological saline or mixtures of physiological saline and for example dimethyl-sulphoxide.

PHARMACOLOGICAL OR PHARMACEUTICAL INFORMATION

The present compounds are suitable for the production of pharmaceutical compositions and preparations. The pharmaceutical compositions or medicaments contain as active material one or more of the present compounds, optionally in admixture with other pharmacologically- or pharmaceutically-active materials. The medicaments are produced in known manner, and known and conventional pharmaceutical auxiliaries and other conventional carriers and diluents can be used.

For example, materials which are recommended and specified in the following literature as auxiliaries for pharmaceutical, cosmetic and related fields can be used as carriers and auxiliaries of this type: Ullmanns Encyklopadie der technischen Chemie, volume 4 (1953) pages 1 to 30; Journal of Pharmaceutical Sciences, volume 52 (1963), pages 918 et seq; H. V. Czetsch-Lindenwald, Hilfsstoffe fur Pharmazie Kosmetik und angrenzende Bebiete, Phar. Ind., volume 2 (1961) pages 72 to seq.; Dr. H. P. Fiedler, Lexikon der Hilfsstoffe fur Pharmazie, Kosmetik und angrenzende Gebiete Cantor KG. Aulendorf in Wurttemberg 1971.

Examples of such materials include gelatin, natural sugars such as sucrose or lactose, lecithin, pectin, starch (for example constarch), gelatin, gum arabic, alginic acid, tylose, talc, lycopodium, silica (for example colloidal silica), glucose cellulose, cellulose derivatives for example cellulose ethers in which the cellulose hydroxyl groups are partially etherified with lower saturated aliphatic alcohols and/or lower saturated oxylalcohols (for example, methyl hydroxypropyl cellulose, methyl cellulose, hydroxyethyl cellulose), hydroxypropyl methyl cellulose, stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils, and fats, especially of plant origin (for example, peanut oil, corn oil, wheat germ oil, sunflower seed oil, cod-liver oil), mono-, di-, and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible polyethylene glycols, mono- or polyvalent alcohols and polyglycols such as glycerine, mannitol, sorbitol, penterythritol, ethyl alcohol, diethylene glycol, triethylene glycol, ethylene glycol, propylene glycol, dipropylene glycol, polyethylene glycol 400 and other polyethylene glylcols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols) or polyhydric alcohols such as glycol, glycerine, diethylene glycol, pentaerythritol, sorbitol, mannitol, ethyl alcohol, butyl alcohol, octadecyl alcohol, etc., e.g. glyceryl stearate, glyceryl palmitate, glycol disterate, glycol dilaurate, glycol diacetate, monoacetin, triacetin, glyceryl stearate, glyceryl palmitate, glycol distearate glycol dilaurate, glycol diacetate, monoacetatin, triacetin, glyceryl oleate, ethylene glycol stearate; such esters of polyvalent alcohols can in a given case, also be etherified, benzyl benzote, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), calcium carbonate, sodium carbonate, calcium phosphate, sodium phosphate, magnesium carbonate and the like.

As further assistants there can also be employed materials which cause disintegration (so-called disintegrants) such as: cross-linked polyvinylpyrrolidone, sodium carboxymethyl starch, sodium carboxymethyl cellulose or microcrystalline cellulose. Likewise, there can be used encapsulating agents such as for example, esters of polyacrylic acid, cellulose ethers and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetin, diacetin, glyceryl monostearate, glyceryl distearate, glyceryl monopalmitate, paraffins, and the like. There can be used for injectable solutions or suspensions for example, non-toxic parenterally compatible diluents or solvents such as for example: 1,3-butanediol, water, Ringer's solution, isotonic sodium chloride solution, (isotonic salt solution) or even hardened oils including synthetic mono or diglycerides or fatty acids such as oleic acid.

In the production of the preparations there can be used known and customary solution aids or emulsifiers. As solution aids and emulsifiers there can be used, for example, polyvinyl pyrrolidone, sorbitan fatty acid esters such as sorbitan trioleate, phosphatides such as lecithin, gum acaia, gum tragacanth, polyoxyethylated sorbitan monooleate and other polyoxyethylated oleotriglycerides, linolized, oleotriglycerides, polyethylene oxide-condensation products of fatty alcohols, alkylphenols or fatty acids, or even 1-methyl-3-(2-hydroxyethyl)imidazolidone-(2). As used herein polyoxyethylated means that the material in question contain polyoxyethylated chains whose degree of polymerization generally is between 2 and 40, particularly between 10 and 20.

Such polyoxyethylated materials for example can be obtained by reaction of hydroxyl group containing compounds (for example, mono-, or diglycerides) or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191-195).

Furthermore, there can be added preservatives, stabilizers, buffers, for example, calcium hydrogen phosphate, colloidal aluminum hydroxide, taste correctives, sweetners, dyes, antioxidants and complex formers (for example, ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium meta bisulfite, ascorbic acid, gallic acid, alkyl gallates, e.g. methyl gallate and ethyl gallate, butyl hydroxyanisole, nordihydroguaiaretic acid, tocopherols as well as tocopherol and synergists (materials which bind heavy metals by complex formation, for example, lecithin, ascorbi acid, phosphoric acid). The addition for synergists increases considerably the antioxidant activity of tocopherol. As preservatives there can be used for example sorbic acid, p-hydroxybenzoic acid esters (for example, lower alkyl esters such as the methyl ester and the ethyl ester) benzoic acid, sodium benzoate, trichloroisobutyl alcohol, phenyl, cresol, benzethonium chloride and formalin derivatives).

The pharmacological and galenical treatment of the compounds of the invention takes place according to the usual standard methods. For example, the active material or materials and assistants or carriers are well mixed by stirring or homogenization (for examplel, by means of a colloid mill or ball mill or other conventional mixing apparatus), wherein the operation is generally carried out at temperatures between 20° and 80° C., preferably 20° to 50° C., especially room temperature. Moreover, reference is made to the following standard work: Sucker, Fuchs, Speiser, Pharmazeutische Technologie, Thieme-Verlag, Stuttgart, 1978).

The present compounds show a good analgesic effect in, for example, the Electropain test, following B. Blake et al, Med. exp. 9, pages 146-150 (1963), Hot-plate test following Janssen and Jageneau, J. Pharm-Pharmacol, 9 page 381 (1957), Tail-flick-test following D'Amour and Smith J. of Pharmacol. and exp. Therap., 72, page 74 (1941), and in the Haffner-test following Haffner, Deutsche Medizinisch Wochenschrift 55, page 731 (1929) and Bianchi and Franceschini, Brit. J. Pharmacol. 9, page 280 (1954).

In the above test methods, for example, the ED50 is 2.8 mg/body weight of mouse per os.

This analgesic effect is comparable to the effect of the known pharmaceutical active material buprenorphine.

The lowest analgesically-active dose in the above animal experiment is for example 1-1.5 mg/kg orally, 0.1-0.15 mg/kg intravenously.

The following is an example of the general range of dose for this effect (animal experiment as above) 1-8 mg/kg orally, 0.1-0.8 mg/kg intravenously.

The pharmaceutical preparations generally contain from 0.1 to 10, preferably from 0.5 to 3 mg of the present active component(s).

The preparation can be dispensed, for example, in the form of tablets, capsules, pills, dragee, suppositories ointments, gels, creams, powder, aerosols or in liquid form. The following examples are possible as liquid forms of application: oily or alcoholic or aqueous solutions and suspensions and emulsions. The most preferred forms of application are tablets which contain from 0.5 to 2 mg or solutions which contain from 1 to 10% of active material.

The individual dose of the present active components can, for example be (a) from 0.1 to 20, preferably from 0.5 to 3 mg in the case of oral forms of the medicaments, (b) from 0.01 to 1, preferably from 0.05 to 0.5 mg in the case of parenteral forms of the medicament (for example intravenous, intramuscular), (c) from 0.05 to 20 mg, preferably from 0.05 go 5 mg, in forms of the medicament intended for rectal or vaginal application.

(The dosages are based in each case on the free base)

By way of example, it is recommended to take three times daily from one to three tablets having a content of from 1 to 3 mg of active material or in the case of for example intravenous injection from one to three times daily one ampoule with a content of from 1 to 10 ml having from 0.1 to 0.5 mg of substance. The administration; the maximum daily dose should not exceed 3 mg in the case of oral administration.

The individual oral dose is generally from about 0.05 to 1 mg/kg of body weight for treating dogs and cats; the parenteral dose is from about 0.01 to 0.2 mg/kg of body weight.

The acute toxicity of the present compounds on the mouse (expressed by the LD 50 mg/kg; method according to Miller and Tainter: Proc. Soc. Exper. Bio. a Med. 57 (1944) 261) is, for example, from 70 to 110 mg/kg (or more than 80 mg/kg) in the case of oral application.

The medicaments can be used in human medicine, veterinary medicine, e.g. in treating dogs, cats, horses, cattle and other mammals and in agriculture either alone or in admixture with other pharmacologically-active materials.

The present compounds are effective analgesics.

Unless otherwise indicated, all parts and percentages are by weight.

The compositions can comprise, consist essentially of, or consist of the materials set forth.

DETAILED DESCRIPTION

EXAMPLES

General procedure for Examples 1 to 21 of Table I using starting compound II, Z representing a halogen atom (chlorine):

0.05 mol 80% sodium hydride are suspended in about 30 ml of the anhydrous solvent which is mentioned (c.f. Table 1). 0.04 mol of the corresponding to formula III (Y=OH) or 0.05 mol of the corresponding mercaptan corresponding to formula III, in which Y represents SH (optionally dissolved in the same solvent) are added dropwise with stirring to room temperature. The reaction commences with the formation of hydrogen. The mixture is heated to 50° C. or, in case a mercaptan is used the mixture is heated to 60° C., and 0.05 mol NaH are dissolved in 50 ml of the solvent used. On completion of the reaction, 0.05 mol of the corresponding chloropyridine (optionally in the same absolute solvent) are added dropwise, preferably at room temperature and the reaction mixture is heated for several hours (from 3 to 6 hours) under reflux (if a mercaptan is used to from 80° to 100° C.). After cooling with water the mixture is hydrolysed and the resulting aqueous solution is extracted more than once with diethylether or methylene chloride. The solvent is distilled off under vacuum after drying over magnesium sulphate and filtration. The working up can be carried out by three different methods:

(A) Purification of the residue by preparative column chromatography on silica gel and optional subsequent salt formation, for example using isopropanolic HCl;

(B) Purification by distillation under vacuum and optional subsequent salt formation as in (A);

(C) If the resulting residue is not unduly impure the salt can be formed without prior purification. The residue is generally dissolved in isopropanol and mixed with isopropanolic hydrochloric acid.

The salt which has crystallized to completion is filtered off and recrystallized in a solvent.

The compounds which are thereby produced corresponding to the following formula are set out in Table 1.

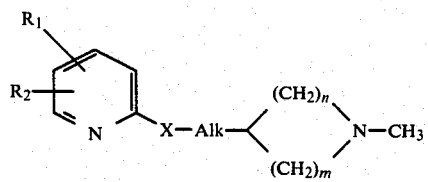

EXAMPLE 22

6-chloro-2-[(N-2-phenylethyl)-piperidyl-(4)-oxy]-pyridine

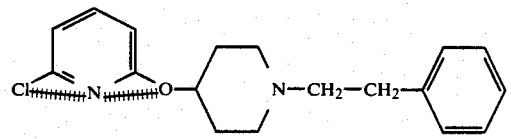

1.3 g of 75% sodium hydride are introduced batchwise with stirring at room temperature into a solution of 8.2 (0.04 mol) of N-(2-phenylethyl)-4-hydroxy-piperidine in 60 ml absolute dimethyl acetamide. On completion of addition, 5.9 g (0.04 mol) of 2.6-dichloropyridine are added. The reaction mixture is heated for 8 hours to from 120° to 130° C. It is then cooled to room temperature and poured into about 300 ml of water. The crystalline product which precipitates is separated off. After stirring in 2N aqueous hydrochloric acid for about one hour, it is drawn off by suction, washed with water, dried, and recrystallized from ethanol. Melting point of the hydrochloride: 253°–254° C.

EXAMPLE 23

6-Chloro-2-[piperidyl-(4)-thio]pyridine

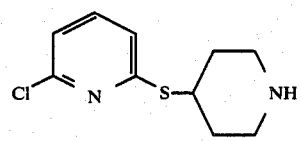

The reaction is carried out under an argon atmosphere. 0.27 g of 80% sodium hydride (0.009 mol) are suspended in 10 ml of dimethylacetamide; the mixture is cooled with ice and then 0.615 g (0.004 mol) of solid 4-mercapto-piperidine-hydrochloride are added and stirred for 10 minutes. A solution of 0.588 g (0.004 mol) of 2,6-dichloro-pyridine in 5 ml of dimethylacetamide are then added dropwise to this mixture and the reac-

TABLE 1

| Example No. | $R_1$ | $R_2$ | X | Alk | n | m | Solvent | Purification variant | m.p. as hydrochloride |
|---|---|---|---|---|---|---|---|---|---|
| 1 | 6-Cl | H | O | — | 2 | 2 | DMSO | C | 186–187° C. |
| 2 | 6-Cl | H | O | — | 3 | 1 | DMSO | C | 180–183° C. |
| 3 | 6-Cl | H | O | CH₂CH₂ | 0 | 3 | DMSO | C | 134–136° C. |
| 4 | 6-Cl | H | O | — | 2 | 3 | DMSO | C | 110–113° C. |
| 5 | 6-Cl | H | O | CH₂ | 0 | 4 | DMAC | C | 147–148° C. |
| 6 | 6-Cl | H | O | CH₂ | 1 | 3 | DMAC | C | 168–169° C. |
| 7 | 6-Cl | 3-NO₂ | O | — | 2 | 2 | DMF | C | 214–216° C. |
| 8 | 6-Cl | 3-NH₂ | O | — | 2 | 2 | dioxon | C | 245–250° C. |
| 9 | 3-NO₂ | H | O | — | 2 | 2 | dioxan | C | 240–241° C. |
| 10 | 6-Cl | 3-NHCOCH₃ | O | — | 2 | 2 | dioxan | C | 226–230° C. |
| 11 | 6-Cl | H | O | — | tropanyl-(3) radical | | DMSO | C | 250–251° C. |
| 12 | 6-Cl | H | O | — | quinuclidyl- | | DMSO | C | 241–243° C. |
| 14 | H | H | S | — | 2 | 2 | DMSO | C | 132–134° C. maleate |
| 15 | 6-Cl | H | S | — | 2 | 2 | DMSO | C | 110–112° C. maleate |
| 16 | 6-Cl | H | S | — | 2 | 2 | DMSO | C | 184–187° C. |
| 17 | 6-CH₃ | H | S | — | 2 | 2 | DMSO | B | 216–218° C. dihydrochloride |
| 18 | 6-OCH₃ | H | S | — | 2 | 2 | DMSO | B | 165–167° C. |
| 19 | 6-Br | H | S | — | 2 | 2 | DMSO | C | 198–199° C. |
| 20 | 5-Cl | H | S | — | 2 | 2 | toluene | C | 134–136° C. maleate* |
| 21 | 3-Cl | H | S | — | 2 | 2 | DMSO | C | 125–126° C. maleate* |

DMSO = dimethylsulphoxide; DMF = dimethylformamide; DMAC = dimethylacetamide
A dash (—) in the Alk column means that there is no Alk group
The maleates of Examples 14 and 15 are produced using isopropanolic maleic acid solution.
*These maleates are produced with maleic acid in acetone and recrystallised from ethanol.

tion mixture is stirred for 2.5 hours at room temperature.

Working up of the reaction mixture: 25 ml of water are added dropwise with cooling, 20 ml of methylene chloride are then added, the organic phase is separated off, the aqueous phase is then extracted twice with 15 ml of methylene chloride each time, the combined organic phase is washed twice, in each case with 10 ml of water, dried with sodium sulphate, the solution is concentrated on a rotary evaporator, the residue is mixed with 10 ml of absolute ethanol and then reconcentrated. About 1.5 ml of a yellow liquid is obtained which is purified by column chromatography with 60 g of silica gel (Geduran Si 60, by Merck, Darmstadt) (charging level of the colum 400 mm diameter of 20 mm). The mixture is then eluted with a mixture of 850 ml of chloroform, 150 ml of ethanol and 10 ml of concentrated aqueous ammonia.

The product which is obtained on removal of the eluant is diluted with 10 ml of ether, an equivalent quantity of HCl in isopropanol is added dropwise and the mixture is placed for several hours in a deep freezer after addition of seed crystals. The hydrochloride of the 6-chloro-2-[piperidyl-(4)-thio]-pyridine which crystallizes out is filtered off with suction, washed with ether and dried under oil pump vacuum at 50° C. Melting point of the hydrochloride 132°–133° C.

The 4-mercaptopiperidine(hydrochloride) can be produced in the following manner for example from 1-methyl-piperidinone-(4):

Hydrogen sulphide is introduced in a vigorous current with stirring into a solution of 1026 g (9.066 mols) of freshly-distilled 1-methyl-piperidinone-(4) in 1.5 liters of isopropanol. The temperature of the reaction mixture is held at hydrogen absorbed in commercial sodium hypochlorite solution. After hydrogen sulphide has been introduced for about two hours the reaction product begins to crystallize from the solution. Gasing is continued for a further two hours. The 1-methyl-piperidine-4-bis(hydrosulphide)-hydrate which is obtained in this manner is filtered off by suction, washed twice, in each case with 300 ml of cold isopropanol, and then washed twice in each case with 500 ml of diethylether. The substance is stored in the dark in a desiccator over phosphorous pentoxide and should then be rapidly processed.

350 g (9.23 mols) of sodium borohydride powder are suspended in 2.5 liters of isopropanol. 1396 g (7.7 mols) of 1-methyl-piperidine-4-bis-(hydrosulphide)-hydrate are added batchwise with stirring. The reaction takes place exothermically. The mixture is cooled with an ice-bath, and the temperature should not exceed 25° C. The hydrogen sulphide which is given off is absorbed in commercial sodium hypochlorite solution. On completion of addition the cooling bath is removed and allowed to stand overnight at room temperature. The reaction mixture is then heated to 80° C. over about 60 minutes by continuously raising the temperature and is held at this temperature for two hours. The isopropanol is substantially distilled off from the descending condenser under a slight vacuum (100 torr).

The paste-like residue is cooled to room temperature and then mixed with 1.5 liters of diethylether. An easily-stirrable suspension is produced. 740 ml of ice water are slowly added dropwise with further cooling. After about half the quantity of water has been added dropwise, the content of the flask once again has been added dropwise, the content of the flask once again has a paste-like consistency which is difficult to stir. Further addition of water again causes improved stirring and a marked separation of the organic phase and the inorganic boranate residue. The stirring is adjusted, and the ether phase is drawn off. The residue is stirred three times, in each case with 500 ml of fresh ether. The combined organic phases are dried over magnesium sulphate. After filtration the solution is concentrated under reduced pressure on a rotary evaporator. The residue under goes vacuum distillation. Owing to the low boiling point (B.P. from 35°–40° C.) the resulting 1-methyl-4-mercapto-piperidine is collected in a vessel which has been cooled with methanol/dry ice.

59.6 g (0.56 mol) of chloroethylformate are added dropwise with stirring at from 15° to 20° C. to a solution of 65.5 g (0.5 mol) of 1-methyl-4-mercapto-piperidine in 300 ml of acetone. The hydrochloride of the 1-methyl-4-ethoxycarbonyl-mercapto-piperidine precipitates as a crystalline product and is drawn off by suction on completion of the reaction, washed with acetone and dried. The base is freed from the salt in aqueous solution with concentrated aqueous ammonia solution. The solution of the base in ether is dried with $Na_2SO_4$, filtered and concentrated. The substance is purified by distillation. B.P. 128°–130° C.

106.3 g (0.88 mol) of chloroethylformate are added dropwise with stirring over a period of 30 minutes to a solution of 100 g (0.48 mol) of 1-methyl-4-ethoxycarbonyl-mercapto-piperidine in 80 ml of toluene which has been heated to 90° C. The solution is then heated for two hours to from 100° to 110° C. After repeated addition of 40 g of chloroethylformate the solution is heated for a further three hours. After leaving it to stand overnight at room temperature it is drawn off by suction using a glass fibre filter. The solution is concentrated on a rotary evaporator and the residue is distilled off. 20 g (94% of the theoretical yield) of 1-ethoxycarbonyl-4-ethoxycarbonyl-mercapto-piperidine are obtained. B.P. 138°–140° C.

269.7 g (1.032 mols) of 1-ethoxycarbonyl-4-ethoxycarbonyl-mercapto-piperidine are dissolved in a mixture of 886 ml (10.3 mols) of concentrated aqueous hydrochloric acid and 443 ml of glacial acetic acid. The mixture is heated with stirring over a period of 1 hour to reflux temperature.

After a reaction time of 60 hours the solution is concentrated on a rotary evaporator.

In order to remove substantially the residual solvent mixture, the crystalline residue is mixed twice with 200 ml of isopropanol in each case. The mixture is then further distilled off. The 4-mercapto-piperidine-hydrochloride which is thereby obtained is recrystallized from ethanol.

M.P. 183°–184° C. (decomposition). The yield is 117.6 g and increases after working-up the mother liquor by a further 27.5 g; that is about 96% of the theoretical yield.

EXAMPLE 24

6-chloro-2-[N-methyl-piperidyl-(4)-thio]-pyridine-N-oxide

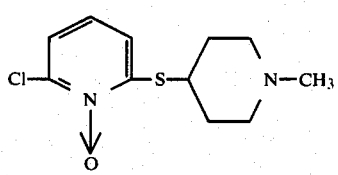

4.9 g (0.03 mol) of 2,6-dichloropyridine-N-oxide are added dropwise to a solution of 4.5 g (0.035 mol) of N-methyl-4-mercapto-piperidine in 20 ml of ethanol. The piperidine compound is in the form of its sodium salt and had been produced using 11.9 g (0.035 mols) of 20% sodium methylate solution.

The reaction mixture is heated to 50° C. and held at this temperature for three hours. The reaction mixture is then poured into about 200 ml of ice water, a crystalline material thereby precipitating. The reaction mixture is filtered several times with suction, subsequently washed with water, dried recrystallized from ethanol. M.P.: 129°–130° C.

The starting material 2,6-dichloro-pyridine-N-oxide is obtained, for example, in the following manner; a solution of 16 g (0.108 mol) of 2,6-dichloro-pyridine and 17 g of 35% perhydrol (corresponding to 5.9 g of active $H_2O_2$, about 0.17 mols) and 250 g of trifluoroacetic acid are heated for 8 hours on a water bath. The internal temperature is about 75° C. The solution is then poured into 1.5 liters of water. A small quantity of a crystalline product precipitates thereby, this being unreacted 2,6-dichloro-pyridine. After filtration with suction of this product, the solution is substantially concentrated under a water jet vacuum at a bath temperature of from 30° to 35° C. The liquid residue is dissolved in 500 ml of chloroform and sufficient anhydrous potash is added with stirring until the formation of gas ceases and in addition the water is bound. By filtration at a bath temperature of from 30°–35° C. and concentration under slight vacuum to dryness 2,6-dichloro-pyridine-N-oxide is obtained as the crystalline residue. M.P. 137°–138° C.

EXAMPLE 25

Production from a compound II, in which Z represents SH or OH and a compound III, in which Y represents halogen:

A mixture of 0.06 mol of a compound corresponding to formula III, in which Y represents halogen and 0.06 mol of 6-chloro-2-mercapto-pyridine-sodium salt in for example 60 ml of n-propanol are heated for several hours (for 6 hours for example) with stirring and under reflux. After cooling insoluble residues are filtered off by suction.

The solution is concentrated and the syrupy residue is acidified with isopropanolic hydrochloric acid. After diluting with acetone the hydrochloride crystalline out.

The crystals are isolated, washed with acetone, and subsequently with water. Further purification is carried out by recrystallization.

The 2-[-N-methyl-piperidyl-(2)-ethyl-mercapto]-6-chloro-pyridine corresponding to the following formula

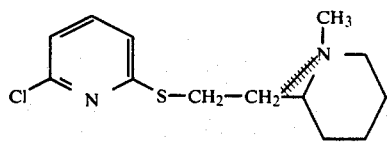

is obtained from 9.3 g of N-methyl-2-(2 chloroethyl)-piperidine and 9.6 g of 2-sodium mercapto-6-chloro-pyridine in the manner described. M.P. of the hydrochloride: 165°–167° C.

Recrystallization is carried out from ethanol/ether. The compounds according to Examples 13–16 of Table I are also produced in this manner.

The 6-chloro-2-mercapto-pyridine can be produced for example, in the following manner:

103.1 g (0.70 mol) of 2,6-dichloropyridine and 110.0 g (2×0.70 mols) of sodium hydrogen sulphide×$H_2O$ (71%) are introduced into 700 ml of n-butanol and heated for a total of 10 hours under reflux. Filtration with suction is carried out at 35° C. and the filtrate is concentrated by evaporation under vacuum at 60° C. (170 g of residue). The residue is mixed with 1 liter of ether and allowed to stand overnight. The solid product which is formed (sodium salt) is drawn off by suction, thoroughly washed with ether and dried for 24 hours under vacuum at 35° C.

Examples 24 to 26 (Table 2) relate to the introduction, by alkylation or acylation of the radical $R_3$ compounds corresponding to formula I, in which $R_3$ represents hydrogen.

General procedure for Examples 24 to 43:

The amine corresponding to formula I, in which $R_3$ represents hydrogen, is heated under reflux with the halide corresponding to the formula $HalR_3$ (excess of the halide of from 10 to 300 mol %) and the base (until no further reaction is observed on analysis by thin layer chromatography). After cooling, filtering off of the precipitate and concentration of the solvent, the mixture is worked-up in conventional manner with salt formation, purification by chromatography on silica gel being necessary in several cases.

The compounds corresponding to the following formula which are produced thereby

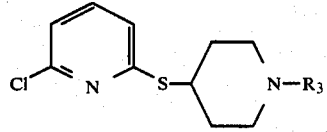

are set out in Table 2.

TABLE 2

| Example No | $R_3$ | Solvent | Basic Compound | Salt | m.p. |
|---|---|---|---|---|---|
| 26 | (CH$_2$)$_2$—⌬ | dioxan | TEA | maleate | 126–127° C. |

TABLE 2-continued

| Example No | R$_3$ | Solvent | Basic Compound | Salt | m.p. |
|---|---|---|---|---|---|
| 27 | CH$_2$CH$_2$=CH$_2$ | dioxan | TEA | oxalate | 134–136° C. |
| 28 | CH$_2$CH$_2$CH | xylene | K$_2$CO$_3$ | base | 67–70° C. |
| 29 | CH$_2$CH$_2$CO—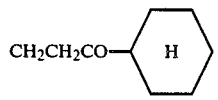 | dioxan | TEA | HCl | 169–173° C. |
| 30 | C$_3$H$_7$ | dioxan | TEA | HCl | 172–175° C. |
| 31 | CH$_2$—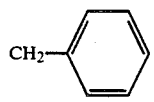 | dioxan | TEA | oxalate | 175–178° C. |
| 32 | n-C$_6$H$_{13}$ | DMA/toluene | NaHCO$_3$ | oxalate | 155–156° C. |
| 33 | C$_2$H$_5$ | dioxan | TEA | HCl | 203–205° C. |
| 34 | CH(CH$_3$)$_2$ | dioxan | TEA | oxalate | 160° C. |
| 35 | CH$_2$CH(CH$_3$)—CH$_3$ | DMAC/toluene | NaHCO$_3$ | maleate | 135–136° C. |
| 36 | CH$_2$CH$_2$CH$_2$F | DMAC/toluene | NaHCO$_3$ | HCl | 167–169° C. |
| 37 | CH$_2$CH$_2$CH$_2$N(CH$_3$)$_2$ | DMAC/toluene | NaHCO$_3$ | HCl | 273–277° C. |
| 38 | 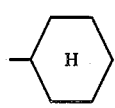 | DMAC/toluene | NaHCO$_3$/K$_2$CO$_3$ | HCl | 205–206° C. |
| 39 | COCH$_3$ | dioxan | TEA | base | 210–215° C. |
| 40 | COCH$_2$CH$_2$—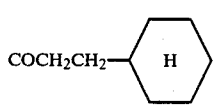 | dioxan | K$_2$CO$_3$ | base | Rf 0,79 |
| 41 | CH$_2$—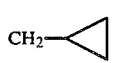 | DMAC | K$_2$CO$_3$ | HCl | 173–175° C. |
| 42 | (CH$_2$)$_2$CH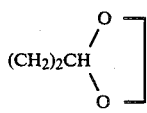 | toluene | NaHCO$_3$/K$_2$CO$_3$ | oxalate | 176–178° C. |
| 43 | (CH$_2$)$_3$—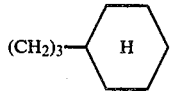 | dioxan | TEA | HCl | 198–201° C. |
| 44 | (CH$_2$)$_2$—O—CH$_3$ | DMAC/toluene | NaHCO$_3$/K$_2$CO$_3$ | base | Rf 0,50 |
| 45 | 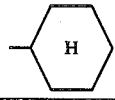 | toluene | NaHCO$_3$ | HCl | 208–210° C. |

TEA = trimethylamine
DMAC = dimethylacetamide

The compounds of Example 40 and 44 do not have a melting point but can be characterized by the R$_f$ values. The R$_f$ value for the compound of Example 40 is 0.79 and the R$_f$ value for the compound of Example 44 is 0.50.

In both cases the mobile phase was chloroform/methanol/25% aqueous ammonia in the ratio 95:4:1 (by volume).

The determination of the R$_f$ value was carried out in a trough chamber with chamber saturation at room temperature: Stationary phase, silica gel having a layer thickness of 0.25 mm (prepared plate Type 60 1254, (Merck); Amount of material applied: about 100 g; Mobile phase: chloroform/methanol/25% NH₃ (95:4:1 by volume); Distance traversed by the solvent: 14 cm. The idenfication was carried out through the following coloring reagents:
1. UV light, 254 nm
2. Iodine
3. HCl, 25%

EXAMPLE 46

2-(N-(2,3-dihydroxy-propyl)-piperidyl-(4)-thio]-6-chloro-pyridine

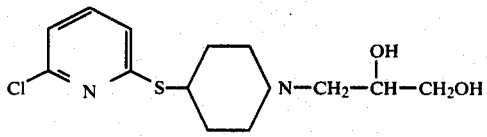

4.85 g (0.0212 mol) of 2-(piperidyl-(4)-thio)-6-chloro-pyridine (free base) are heated together with 1.4 ml of glycidol and 40 ml of isopropanol for 5 hours to boiling point. The isopropanolic solution is concentrated and mixed with 6 ml of isopropanolic HCl. The hydrochloride slowly crystallizes out. M.P. of the hydrochloride: 115°–121° C.

EXAMPLE 47

2-[N-methyl-piperidyl-(4)-oxy]-3-acetylamino-6-(4-fluoro-benzylamino)-pyridine

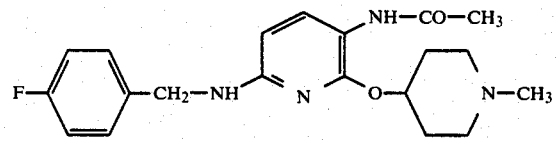

1.8 ml of acetyl chloride are added under nitrogen to the hydrogenation solution of 0.025 mol of 2-[N-methyl-piperidyl-(4)-oxy]-3-amino-6-(4-fluoro-benzylamino)-pyridine, which is obtained by hydrogenating 4.5 g (0.025 mol) of the corresponding 3-nitro compound in 125 ml of dioxan in the presence of a palladium-carbon catalyst at 60° C. and under a pressure of 5 bars. The hydrochloride which precipitates is filtered off with suction and the base is freed in conventional manner with sodium hydroxide solution. M.P. of the hydrochloride: 188°–190° C.

EXAMPLE 48

2-[N-methyl-piperidyl-(4)-oxy]-3-ethoxycarbonylamino-6-(4-fluoro-benzylamino)-pyridine

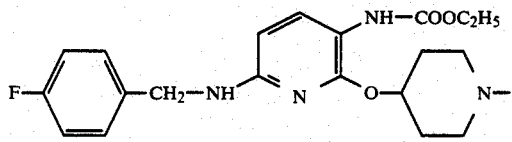

4 ml of chloroformic acid ethyl ester are added dropwise with stirring and under a nitrogen atmosphere to a hydrogenation solution of 0.02 mol of 2-[N-methyl-piperidyl-(4)-oxy]-3-amino-6-(4-fluoro-benzylamino)-pyridine which is obtained by hydrogenating 7.2 g (0.02 mol) of the corresponding 3-nitro compound in 125 ml of dioxan in the presence of a palladium-carbon catalyst at 60° C. and under a pressure of 5 bars. The solution is stirred for ½ hour at room temperature, the solution is concentrated and the residue is stirred with a benzene-ether mixture 1:1. The material which has crystallized out is filtered off with suction and recrystallized from methanol. M.P. of the dihydrochloride is from 202°–207° C.

The free base is oabtained from the dihydrochloride by treating with sodium hydroxide solution for example. M.P. of the base is from 168° to 169° C. (without re-crystallization).

EXAMPLES 49–55 (TABLE 3)

These Examples relate to the substitution of a methyl group on the piperidine ring of compounds corresponding to formula I ($R_3=CH_3$) by an ethoxycarbonyl group and the subsequent splitting off of the latter.

General Procedure 0.09 mol of a compound corresponding to formula I, in which $R_3$ represents $CH_3$, are dissolved in 30 ml of toluene and added dropwise with stirring over a period of 30 minutes to a solution of 0.18 mol of chloroformic acid ethylester in 30 ml of toluene which has been heated to 85° C. On completion of dropwise addition, the solution is heated for a further 6 hours with stirring and under reflux, solid constituents are filtered off after cooling and the solution is concentrated to dryness. The resulting N-carbethoxy product is not generally further purified and is used in the form of a crude product. The crude product (compound corresponding to formula I, in which $R_3$ represents $CO—O_2H_5$) is dissolved in a mixture of 80 g of concentrated aqueous hydrochloric acid and 40 ml of glacial acetic acid. The solution is heated for 15 hours under reflux. It is then concentrated to dryness, the residue is mixed with isopropanol and once again concentrated. The solid residue is purified by recrystallization. The compounds which are produced corresponding to the following formula

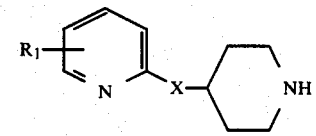

are set out in Table 3.

TABLE 3

| Example No | R₁ | X | Salt | m.p. |
|---|---|---|---|---|
| 49 | 6-Cl | O | HCl | 219–220° C. |
| 50 | 6-Cl | S | maleate | 144–145° C. |
| 52 | H | S | 2HCl | 256–257° C. |
| 53 | 6-CH₃ | S | 2HCl | 243–244° C. |
| 54 | 5-Cl | S | HCl | 211–212° C. |
| 55 | 3-Cl | S | HCl | 201–202° C. |

EXAMPLE 56

(Substitution of a methyl group on the piperidine ring by ethoxy-carbonyl and splitting off of the latter)
6-chloro-2-[piperidyl-(4)-thio]-pyridine-N-oxide

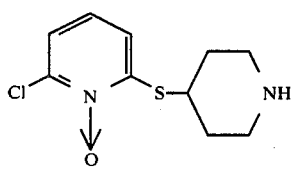

A solution of 3.5 g of 2-[1-methylpiperidine-4-mercapto]-6-chloro-pyridine-N-oxide in 20 ml of chloroformic acid ethylester is heated with stirring and under reflux. After 3 hours a further 20 ml of chloroformic acid ethylester are added in each case (repeated 3 times). The total heating time is therefore 9 hours. The solution is then concentrated to dryness. The solid residue is recrystallized from ethanol.

The 6-chloro-2-[N-carbethoxy-piperidyl-(4)-thio]-pyridine which is thus obtained melts at a temperature of from 151° to 152° C.

2.4 g (0.0075 mol) of this carbethoxy compound are heated for 16 hours with stirring and under reflux with 7.6 g of concentrated aqueous HCl (0.075 mol) and 5 ml of glacial acetic acid. The solution is subsequently concentrated and the crystalline residue is mixed with 25 ml of methanol. It is once again concentrated to dryness. The residue is subsequently dissolved in the necessary quantity of methanol at boiling temperature. The solution is filtered following addition of kieselguhr, and the solution is then mixed with ether until it begins to cloud. The 6-chloro-2-[piperidyl-(4)-thio]-pyridine-N-oxide-hydrochloride crystallizes out. After standing for one hour in an ice bath, the filtrate is filtered off with suction, and the crystalline product is washed with acetone and dried. M.P. of the hydrochloride 232°–233° C. (decomposition)

EXAMPLE 57

2-[N-methyl-piperidyl-(4)-oxy]-3-nitro-6-(4-fluorobenzyl-amino)-pyridine

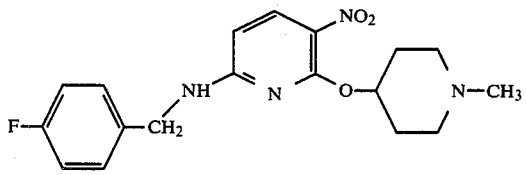

31 g (0.114 mol) of 2-[N-methyl-piperidyl-(4)-oxy]-3-nitro-6-chloro-pyridine, 15.6 g (0.125 mol) of 4-fluorobenzylamine, 34.5 ml (0.125 mol) of triethylamine and 70 ml of isopropanol are heated for 7 hours under reflux. The triethyl ammonium chloride which precipitates after cooling is separated off and the mother liquor is concentrated under vacuum. The title compound crystallizes out in the form of the free base and is filtered off with suction and dried. M.P. from 90°–94° C.

EXAMPLE 58

2-[N-methyl-piperidyl-(4)-oxy]-3-amino-6-(4-fluorobenzylamino)-pyridine

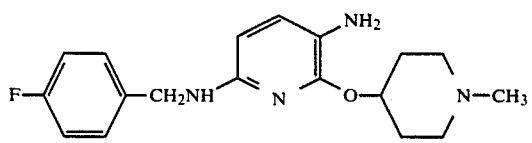

4.5 g (0.0125 mol) of 2-[N-methyl-piperidyl-(4)-oxy]-3-nitro-6-(4-fluoro-benzylamino)-pyridine and 0.6 g of palladium on active carbon (5%) are suspended in 125 ml of dioxan and hydrogenated for 5 hours at 60° C. and under a pressure of 5 bars in a hydrogenative apparatus. After removing the catalyst, the solution is mixed with excess isopropanolic HCl. The dihydrochloride while precipitating is filtered off with suction and recrystallized from ethanol with addition of small quantity of ether. M.P. of the dihydrochloride from 245° to 248° C.

EXAMPLE 59

2-[N-methyl-piperidyl-(4)-thio]-6-chloro-pyridine-sulphoxide and -sulphone 5 g (0.018 mol) of 2-[N-methyl-piperidyl-(4)-thio]-6-chloro-pyridine-hydrochloride are dissolved in 50 ml of methanol. The pH value is adjusted to pH 4 using 1N aqueous hydrochloric acid and the solution is heated to 50° C., 2.4 g (about 0.021 mol) of 30% H₂O₂ are added dropwise with stirring. The reaction mixture is heated to boiling. After about 2 hours, a further 2.4 g of 30% H₂O₂ are added. After a total reaction time of 16 hours, excess H₂O₂ is destroyed by addition of concentrated formic acid. The solution is concentrated at room temperature and the syrupy residue is dissolved in a small quantity of water. The solution is made alkaline with concentrated sodium hydroxide solution and the free base is isolated by repeated extraction with ether. After drying of the organic phase the solvent is distilled off under vacuum, the crystalline residue is purified by column chromatography on silica gel (eluant CHCl₃/methanol/ammonia 90:9:1). Two materials are isolated:

1. 400 mg of sulphone m.p. 123°–124° C.
2. 2.3 g of sulphoxide m.p. 136°–137° C.

A relatively large yield of sulphone can for example be obtained in the following manner:

3 g (0.012 mol) of 2-[N-methyl-piperidyl]-(4)-thio]-6-chloro-pyridine are dissolved in 30 ml of glacial acetic acid. A solution of 3.5 g (0.022 mol) of potassium permanganate in 50 ml of water are added dropwise (over a period of 60 minutes) with stirring at 40° C. On completion of dropwise addition the solution is heated for 2 hours to 60° C. The precipitate which is formed is filtered off and the solution is concentrated to dryness. The resulting crystalline residue is stirred with ether and filtered off with suction. M.P.: 124°–125° C.

EXAMPLES OF PHARMACEUTICAL PREPARATIONS

EXAMPLE 1: CAPSULES 50 g active material are mixed with 350 g of microcrystalline cellulose, 590 g of lactose and 10 g of magnesium stearate.

100 mg of the mixture are in each case filled into solid size 3 gelatin capsules.

One capsule contains 5 mg of active material.

EXAMPLE 2: AMPOULES 10 g of active material are dissolved together with 30.48 g of sodium chloride in about 3.8 liters of water suitable for injection. The solution which is obtained is adjusted to pH 7.4 with 0.1N of sodium hydroxide solution and is filled up to the 4 liter mark with water suitable for injection. The solution is filtered in sterile manner through a membrane filter having suitable pore width. Ampoules are filled to 2 ml with the filtrate under a septic condition. The ampoules are then sterilized for 20 minutes in steam at 121° C.

One ampoule contains 5 mg of active material in 2 ml of solution.

The entire disclosure of German priority application P No. 3347276.9 is hereby incorporated by reference.

What is claimed is:

1. A compound corresponding to the formula

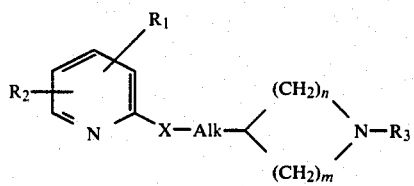

wherein the radicals $R_1$ and $R_2$ represent hydrogen, halogen atoms, a trifluoromethyl group, a cyano-group, a nitro group, an amino group, a mono-$C_1$-$C_6$-alkylamino group, a di-$C_1$-$C_6$-alkylamino group, an amino group which is substituted by a phenyl radical, a mono- or di-halophenyl radical or a phenyl-$C_1$-$C_4$-alkyl radical, a $C_1$-$C_6$ alkanoyl amino group, a $C_1$-$C_6$ alkoxycarbonylamino group, a $C_1$-$C_6$ alkyl group, a $C_1$-$C_6$ alkyl group substituted by a phenyl radical, a phenyl group, a hydroxy group, a $C_1$-$C_6$ alkoxy group, a phenoxy group, a carboxy group, a carb-$C_1$-$C_6$-alkoxy group, a carbamoyl group, or a carbamoyl group which is optionally substituted by one or two $C_1$-$C_6$ alkyl groups, the radical $R_3$ represents hydrogen, a $C_1$-$C_6$ alkyl group, a $C_3$-$C_6$ alkenyl group, a $C_3$-$C_6$ alkynyl group, a $C_3$-$C_7$-cycloalkyl group, a $C_5$-$C_7$ cycloalkenyl group, a phenyl-$C_1$-$C_4$-alkyl group, a carb-$C_1$-$C_6$-alkoxy group, a $C_2$-$C_6$-alkanoyl group, a $C_2$-$C_6$-alkanoyl group substituted by a $C_3$-$C_6$-cycloalkyl radical or a $C_1$-$C_4$ alkyl group which contains on the same carbon atom two $C_1$-$C_6$ alkoxy groups or $C_2$-$C_4$ alkylene dioxy group, or wherein $R_3$ represents a $C_1$-$C_6$ alkyl group which is mono- or di-substituted by $C_3$-$C_7$ cycloalkyl group, hydroxy group, $C_1$-$C_6$ alkoxy group, halogen atom, sulpho group ($-SO_3H$), amino group, $C_1$-$C_6$ alkylamino group, di-$C_1$-$C_6$-alkylamino group, $C_1$-$C_6$ alkylcarbonyl group, $C_3$-$C_7$ cycloalkylcarbonyl group, carb-$C_1$-$C_6$-alkoxy group or benzoyl group, X represents oxygen, sulphur, SO or $SO_2$, Alk represents a direct bond or alkylene having from 1 to 4 carbon atoms and n and m are integers from 1 to 3, n can also be 0 if Alk is alkylene having at least one carbon atom and in this case m is from 2 to 6; and the group

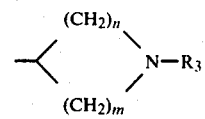

which is always cyclic can also be a quinuclidyl radical or a tropanyl radical, the pyridine-N-oxide, amine oxide or mixed pyridine-N-oxide amine oxide thereof or a pharmaceutically acceptable salt thereof with the proviso that when $R_1$ and $R_3$ are hydrogen $R_2$ is not hydrogen or a $C_1$-$C_6$ alkyl group.

2. A compound according to claim 1 having the formula

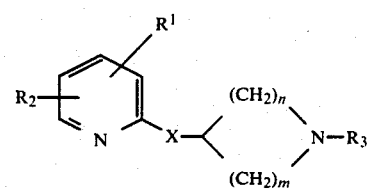

where $R_1$ is hydrogen, amino or $C_2$-$C_6$-alkanoylamino, $R_2$ is chlorine, bromine, fluorine, $C_1$-$C_4$-alkyl or $C_1$-$C_4$-alkoxy, X is sulphur and $R_3$ is hydrogen, $C_3$-$C_6$-alkenyl, $C_1$-$C_6$-alkyl or $C_1$-$C_6$-alkyl substituted with a halogen atom, a methylenedioxy group or one or two hydroxy groups, and wherein the basic saturated ring

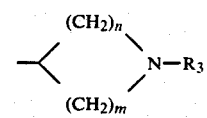

is a pyrrolidyl group, a piperidyl group or a homopiperidyl group which in each case on the N-atom contains the group $R_3$ or a pharmaceutically acceptable salt thereof.

3. A compound according to claim 2 wherein $R_1$ is hydrogen, $R_2$ is chlorine, bromine, or fluorine and $R_3$ is hydrogen or a $C_1$-$C_6$-alkyl group.

4. A compound according to claim 1 wherein X is oxygen.

5. A compound according to claim 1 wherein X is sulfur.

6. A compound according to claim 1 wherein $R_2$ is chlorine.

7. A pharmaceutical composition comprising as active material a compound according to claim 1 in an analgesically effective amount together with a pharmaceutical carrier or diluent.

8. A method of relieving pain comprising administering to a mammal in need of analgesic treatment an analgesically effective amount of a compound corresponding to the formula

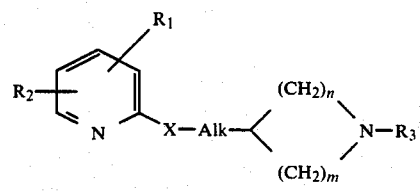

wherein the radicals $R_1$ and $R_2$ represent hydrogen, halogen atoms, a trifluoromethyl group, a cyano group, a nitro group, an amino group, a mono-$C_1$-$C_6$-alkylamino group, a di-$C_1$-$C_6$-alkylamino group, an amino group which is substituted by a phenyl radical, a mono- or di-halophenyl radical or a phenyl-$C_1$-$C_4$-alkyl radical, a $C_1$-$C_6$ alkanoyl amino group, a $C_1$-$C_6$ alkoxycarbonylamino group, a $C_1$-$C_6$ alkyl group, a $C_1$-$C_6$ alkyl group substituted by a phenyl radical, a phenyl group, a hydroxy group, a $C_1$-$C_6$ alkoxy group, a phenoxy group, a carboxy group, a carb-$C_1$-$C_6$-alkoxy group, a carbamoyl group, or a carbamoyl group which is optionally substituted by one or two $C_1$-$C_6$ alkyl groups, the radical $R_3$ represents hydrogen, a $C_1$-$C_6$ alkyl group, a $C_3$-$C_6$ alkenyl group, a $C_3$-$C_6$ alkynyl group, a $C_3$-$C_7$-cycloalkyl group, a $C_5$-$C_7$ cycloalkenyl group, a phenyl-$C_1$-$C_4$-alkyl group, a carb-$C_1$-$C_6$-alkoxy group, a $C_2$-$C_6$-alkanoyl group, a $C_2$-$C_6$-alkanoyl group substituted by a $C_3$-$C_6$-cycloalkyl radical or a $C_1$-$C_4$ alkyl group which contains on the same carbon atom two $C_1$-$C_6$ alkoxy groups or $C_2$-$C_4$ alkylene dioxy group, or wherein $R_3$ represents a $C_1$-$C_6$ alkyl group which is mono- or di-substituted by $C_3$-$C_7$ cycloalkyl group, hydroxy group, $C_1$-$C_6$ alkoxy group, halogen atom, sulpho group ($-SO_3H$), amino group, $C_1$-$C_6$ alkylamino group, di-$C_1$-$C_6$-dialkylamino group, $C_1$-$C_6$ alkylcarbonyl group, $C_3$-$C_7$ cycloalkylcarbonyl group, carb-$C_1$-$C_6$-alkoxy group or benzoyl group, X represents oxygen, sulphur, SO or $SO_2$, Alk represents a direct bond or alkylene having from 1 to 4 carbon atoms and n and m are integers from 1 to 3, n can also be 0 if Alk is alkylene having at least one carbon atom and in this case m is from 2 to 6; and the group

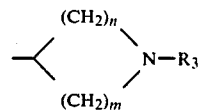

which is always cyclic can also be a quinuclidyl radical or a tropanyl radical, the pyridine-N-oxide, amine oxide or mixed pyridine-n-oxide amine oxide thereof or a pharmaceutically acceptable salt thereof.

9. A method of relieving pain comprising administering to a mammal in need of analgesic treatment an analgesically effective amount of a compound according to claim 2.

10. A method of relieving pain comprising administering to a mammal in need of analgesic treatment an analgesically effective amount of a compound according to claim 3.

11. A method of relieving pain comprising administering to a mammal in need of analgesic treatment an analgesically effective amount of a compound according to claim 4.

12. A method according to claim 8 wherein the compound is administered orally.

13. A method according to claim 8 wherein the compound is administered parenterally.

* * * * *